US006794368B1

(12) United States Patent
Phillips et al.

(10) Patent No.: US 6,794,368 B1
(45) Date of Patent: *Sep. 21, 2004

(54) COMPOSITION AND METHOD FOR INDUCING APOPTOSIS IN PROSTATE CANCER CELLS

(75) Inventors: Nigel C. Phillips, Pointe-Claire (CA); Mario C. Filion, Laval (CA)

(73) Assignee: Bioniche Life Sciences Inc., Belleville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/937,643

(22) PCT Filed: Mar. 30, 2000

(86) PCT No.: PCT/CA00/00342

§ 371 (c)(1),
(2), (4) Date: Jan. 10, 2002

(87) PCT Pub. No.: WO00/59518

PCT Pub. Date: Oct. 12, 2000

Related U.S. Application Data

(60) Provisional application No. 60/127,451, filed on Apr. 1, 1999.

(51) Int. Cl.[7] .............................................. A61K 48/00
(52) U.S. Cl. .................... 514/44; 424/93.1; 424/197.11
(58) Field of Search ...................... 514/2, 44; 424/936, 424/93.1, 193.1, 197.11

(56) References Cited

U.S. PATENT DOCUMENTS 6,326,357 B1 * 12/2001 Phillips et al. ................ 514/44
6,329,347 B1 * 12/2001 Phillips et al. ................ 514/44

FOREIGN PATENT DOCUMENTS

| WO | WO 99/07383 | 2/1999 |
| WO | WO 00/33875 | 6/2000 |

OTHER PUBLICATIONS

Anderson W.F. Human Gene Therapy. Nature 1998, vol. 392 (Suppl.), pp. 25–30.*

Greco O. Cancer gene therapy: 'delivery, delivery, delivery'. Frontiers in Bioscience 2002, vol. 7, pp. d1516–1524.*

Filion M.C. Therapeutic potential of mycobacterial cell wall–DNA complexes. Expert Opinion on Investigational Drugs 2001, vol. 10, pp. 2157–2165.*

Morales, A., et al., "*Immunotherapy of an Experimental Adenocarcinoma of the Prostate*", The Journal of Urology, May 1995, pp. 1706–1710, vol. 153.

Filion, M.C., et al., "*Mycobacterium phlei cell wall complex, a new anti–tumoral agent, induces IL–12 synthesis by monocyte/macrophages via associated DNA*", Blood, Nov. 15, 1997, p. 58b (2959), vol. 90, No. 10, Suppl. 1. (Abstract).

Filion, M.C., et al., "*Mycobacterial cell wall—DNA complex induces apoptosis in cancer cells*", Journal of Pharmacy and Pharmacology, Sep. 1998, p. 39, vol. 50, Supplement. (Abstract).

Filion, M.C., et al., "*Mycobacterium phlei cell wall complex dirctly induces apoptosis in human bladder cancer cells*", British Journal of Cancer, Jan. 1999, pp. 229–235, vol. 79, No. 2.

* cited by examiner

Primary Examiner—Dave T. Nguyen
Assistant Examiner—Jon Eric Angell
(74) Attorney, Agent, or Firm—Kilpatrick Stockton LLP

(57) ABSTRACT

The present invention relates to a composition and method useful for regulating cell proliferation and cell death in a multicellular organism. The present invention particularly relates to a composition comprising a bacterial DNA (B-DNA) and a first pharmaceutically acceptable carrier, wherein the B-DNA induces a response in responsive cells of an animal. The present invention more particularly relates to a composition comprising a mycobacterial DNA (M-DNA) and a first pharmaceutically acceptable carrier, wherein the M-DNA inhibits proliferation of responsive cells of an animal, induces apoptosis in responsive cells of an animal, and stimulattes responsive cells of the immune system of an animal to produce bioactive molecules. Methods of making the M-DNA composition and methods of using the M-DNA composition also are disclosed.

33 Claims, 6 Drawing Sheets

Control PC-3 untreated

PC-3 + MCC 200 µg/ml

COMPOSITION AND METHOD FOR INDUCING APOPTOSIS IN PROSTATE CANCER CELLS

CROSS REFERENCE TO RELATED APPLICATIONS

This application claims priority to U.S. Provisional Application Serial No. 60/127,451 filed Apr. 1, 1999.

FIELD OF INVENTION

The present invention relates to a method for treating prostate cancer.

BACKGROUND OF THE INVENTION

Cancer is an aberrant net accumulation of atypical cells, which can result from an excess of proliferation, an insufficiency of apoptosis, or a combination of the two. Apoptosis is an active cellular death process characterized by distinctive morphological changes that include condensation of nuclear chromatin, cell shrinkage, nuclear disintegration, plasma membrane blebbing, and the formation of membrane-bound apoptotic bodies (Wyllie et al. Int. Rev. Cytol. 68:251, 1980). A molecular hallmark of apoptosis is degradation of the cell's nuclear DNA into oligonucleosomal-length fragments as the result of activation of endogenous endonucleases (Wyllie A. H. Nature 284:555, 1981).

Prostate cancer is a major cause of cancer deaths among the male population. For patients with capsule confined prostate cancer, radical prostatectomy, radiotherapy, a combination of the two, and brachytherapy with radiolabeled seed implants are the most common treatments. Radical prostatectomy can result in impotence and incontinence. Radiotherapy is associated with prostate specific antigen (PSA) recurrence. Brachytherapy can be used only in carefully selected patients.

For patients with extracapsular tumors and metastases, androgen ablation and chemotherapy are the most common treatments. Androgen ablation, for use in patients with androgen-dependent prostate cancer, includes surgical castration (bilateral orchiectomy) and chemical castration using anti-androgens and leutinizing hormone production suppressors. Many patients refuse orchiectomy. Anti-androgens and leutinizing hormone production suppressors, used together to effect total androgen blockade, result in androgen withdrawal symptoms and, also, are very expensive. Moreover, the response to androgen ablation therapy is finite and lasts a medium of 12 to 16 months (Crawford et al. New Eng. J. Med. 321:419, 1989). Enhanced programmed cell death or apoptosis has been identified as a desirable therapeutic outcome in the treatment of prostate cancer (Kyprianou et al., Cancer Surv. 11:265, 1991). Mutations in p53, a protein that is implicated in the control and induction of apoptosis, are associated with poor clinical prognosis and decreased efficacy of a wide range of therapeutic agents used in the treatment of cancer (Chang et al., J. Clin. Oncol. 13:1009, 1995). p53 gene mutation, which results in the accumulation of non-functional p53 protein, is known to be associated with a lack of responsiveness to androgen ablation therapy in the treatment of prostate cancer (Navone et al., J. Natl. Cancer Inst. 85:1657, 1993).

Therapeutic agents that are effective in inhibiting the proliferation of and inducing apoptosis in cancer cells in vitro are recognized as having therapeutic utility for the in vivo treatment of cancer (Furukawa et al., J. Surg. Oncol. 48:188, 1991). For example, the anti-proliferative activity in vitro of chemotherapeutic agents towards prostate adenocarcinoma cancer cells has been shown to positively correlate with their in vivo anti-cancer activity (Pienta et al., Prostate 26:270, 1995). The activity of many of these therapeutic agents is however influenced by p53 mutation status, and those agents whose mechanism of action appears to be independent of p53 are non-selective and highly toxic. Chemotherapy, for use in patients with androgen-independent (hormone refractory) prostate cancer, has palliation as its primary goal. However, the toxic side effects of chemotherapy are debilitating, often dose limiting, and compromise the quality of the patient's life.

Castration or androgen ablation therapy (either alone or in combination) induces apoptosis in prostate tumors. The amount of apoptosis occurring in prostate tumors after androgen ablation has been correlated with p53 status (Westin et al., Am. J. Pathol. 146:1368, 1995). However, almost all patients with metastatic prostate cancer will escape first-line androgen ablation therapy. The induction of apoptosis in prostatic adenocarcinoma following androgen ablation is associated with infiltrating immune effector cells such as cytotoxic T cells and activated macrophages (Landstrom and Funa, Int. J. Cancer 71:451, 1997). The activation of the innate and acquired immune systems, in addition to inhibition of prostate cancer cell proliferation, would be beneficial for the treatment of prostate cancer.

Therefore, there is a need for a novel therapeutic agent for treating prostate cancer that is simple and relatively inexpensive to prepare, that remains therapeutically stable over time, that is effective in the presence of mutated p53, that is capable of stimulating the innate and or the acquired immune system and that is effective at dose regimens that are associated with minimal toxicity even upon repeated administration.

SUMMARY OF THE INVENTION

The present invention satisfies the above need by providing a method for treating prostate cancer in an animal, including a human, wherein a composition comprising *Mycobacterium phlei* (*M. phlei*) DNA (M-DNA) and M-DNA, wherein the M-DNA is preserved and is complexed with the *M. phlei* cell wall (MCC), is administered to the animal in need of such treatment in an amount effective to have an anti-neoplastic effect on cancer cells in the prostate of the animal.

M-DNA and MCC are simple and relatively inexpensive to prepare, their activities are reproducible among preparations, they remain therapeutically stable over time, and they are effective at dose regimens that are associated with minimal toxicity even upon repeated administration.

To prepare MCC, *M.phlei* are grown in liquid medium and harvested. The *M. phlei* are disrupted, and the solid components of the disrupted *M. phlei* are collected by centrifugal sedimentation. The solid components are deproteinized, delipidated, and washed. M-DNA is purified from MCC or is purified directly from *M. phlei*. DNase-free reagents are used to minimize DNA degradation (preserve DNA) during preparation of MCC and M-DNA.

A composition comprising M-DNA or MCC and a pharmaceutically acceptable carrier is administered to an animal, including a human, having prostate cancer in an amount effective to prevent, treat or eliminate prostate cancer cells in the animal, including the human, having prostate cancer. Optionally, additional therapeutic agents including, but not limited to, anti-androgens, chemotherapeutic agents, immunomodulatory agents and steroids can be administered with the M-DNA and MCC. The unexpected and surprising ability of M-DNA and of MCC to prevent, treat or eliminate prostate cancer cells addresses a long felt unfulfilled need in the medical arts and provides an important benefit for animals, including humans.

Accordingly, it is an object of the present invention is to provide a composition and method effective to prevent prostate cancer.

Another object of the present invention is to provide a composition and method effective to prevent hormone sensitive prostate cancer.

Another object of the present invention is to provide a composition and method effective to prevent hormone insensitive prostate cancer.

Another object of the present invention is to provide a method effective to treat prostate cancer.

Another object of the present invention is to provide a method effective to treat hormone sensitive prostate cancer.

Another object of the present invention is to provide a method effective to treat hormone insensitive prostate cancer.

Another object of the present invention is to provide a method effective to eliminate prostate cancer.

Another object of the present invention is to provide a method effective to eliminate hormone sensitive prostate cancer.

Another object of the present invention is to provide a method effective to eliminate hormone insensitive prostate cancer.

Another object of the present invention is to provide a method that has an anti-neoplastic effect on prostate cancer cells.

Another object of the present invention is to provide a method that has an anti-neoplastic effect on hormone-sensitive prostate cancer cells.

Another object of the present invention is to provide a method that has an anti-neoplastic effect on hormone-insensitive prostate cancer cells.

Another object of the present invention is to provide a method effective to inhibit proliferation of prostate cancer cells.

Another object of the present invention is to provide a method effective to inhibit proliferation of prostate cancer cells.

Another object of the present invention is to provide a method effective to inhibit proliferation of hormone sensitive prostate cancer cells.

Another object of the present invention is to provide a method effective to inhibit proliferation of hormone insensitive prostate cancer cells.

Another object of the present invention is to provide a method effective to induce apoptosis in prostate cancer cells.

Another object of the present invention is to provide a method effective to induce apoptosis in hormone sensitive prostate cancer cells.

Another object of the present invention is to provide a method effective to induce apoptosis in hormone insensitive prostate cancer cells.

Another object of the present invention is to provide a method effective to potentiate the activity of other therapeutic agents in the treatment of prostate cancer.

Another object of the present invention is to provide a method effective to potentiate the anti-neoplastic effect of anti-androgenic agents in the treatment of prostate cancer.

Another object of the present invention is to provide a method effective to potentiate the anti-neoplastic effect of chemotherapeutic agents in the treatment of prostate cancer.

Another object of the present invention is to provide a method effective to potentiate the anti-neoplastic effect of radiation in the treatment of prostate cancer.

Another object of the present invention is to provide a method that maintains its effectiveness over time.

These and other objects, features and advantages of the present invention will become apparent after a review of the following detailed description of the disclosed embodiment and the appended claims.

DETAILED DESCRIPTION OF THE INVENTION

Figure 1:
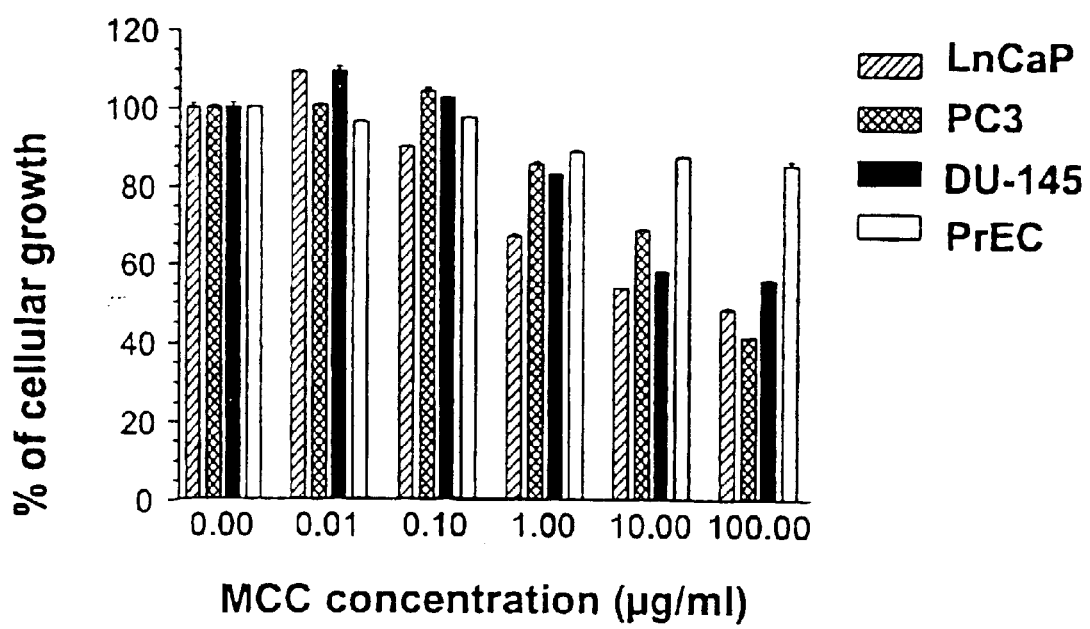
FIG. 1. Inhibition of proliferation of human prostate cancer cells by MCC.

The present invention provides a method for treating prostate cancer in an animal, including a human, wherein a composition comprising a mycobacterial DNA (B-DNA) and B-DNA, wherein the B-DNA is preserved and complexed on a mycobacterial cell wall (BCC), is administered to the animal in need of such treatment in an amount effective to have an anti-neoplastic effect on cancer cells in the prostate of the animal. More particularly, the present invention provides a method for treating prostate cancer in an animal, including a human, wherein a composition comprising *Mycobacterium phlei* (*M. phlei*) DNA (M-DNA) and M-DNA, wherein the M-DNA is preserved and complexed on the *M. phlei* cell wall (MCC), is administered to the animal in need of such treatment in an amount effective to have an anti-neoplastic effect on cancer cells in the prostate of the animal.

As used herein, the term "preserved" refers to DNA that has not been degraded into individual bases.

As used herein, the phrase "complexed on" refers to the physical association of M-DNA with *M. phlei* cell wall.

As used herein, the word "response" refers to inhibition of proliferation of cancer cells, induction of apoptosis in cancer cells, and stimulation of bioactive molecule production by immune system cells.

As used herein, the phrase "bioactive molecules" refers to cytokines and reactive oxygen species.

As used herein, the phrase "immune system cells" refers to macrophages, monocytes, leukocytes, T-cells, B-cells, NK cells, dendritic cells, Langerhan cells, interstitial cells and support cells.

Many bacterial species can be used to practice the present invention including, but not limited to, Coryneform species, Corynebacterium species, Rhodococcus species, Eubacterium species, Bordetella species, Escherichia species, Listera species, Nocardia species and Mycobacterium species.

Preferably, a Mycobacterium species is used including, but not limited to, *M. smegmatis, M. fortuitum, M. kansaii, M. tuberculosis, M. bovis, M. vaccae, M. avium* and *M. phlei*. Most preferably, the Mycobacterium species *M. phlei* is used.

Methods to increase anti-neoplastic activity include, but are not limited to, chemically supplementing or biotechnologically amplifying the M-DNA and MCC with stimulatory sequences or confirmations of DNA derived from the same or different bacterial species; supplementing the M-DNA and MCC with naturally occurring or chemically-synthesized nucleic acids; and, complexing the M-DNA and MCC to natural or synthetic carriers.

Optionally, therapeutic agents including, but not limited to, anti-androgenic, chemotherapeutic, steroidal and immunological agents can be included in the M-DNA and MCC composition of the present invention. M-DNA or MCC and an optional therapeutic agent can be administered simultaneously or sequentially on the same or different schedules.

Anti-androgenic agents include, but are not limited to, flutamide, bicalutamide, nilutamide, megestrol acetate, adrenocorticotropic hormone secretion inhibitors, ketoconazole, estrogens, anti-estrogens and LHRH production suppressors.

Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metaloproteinase inhibiting, CDK inhibiting, caspase inhibiting, proteaosome inhibiting, angiogenesis inhibiting, differentiation inducing and immunotherapeutic drugs. These agents include, but are not limited to, anthracycline antibiotics such as doxorubicin and mitoxantrone, estramustine, vinblastine, paclitaxel, etoposide, cyclophosphamide, cisplatin, carboplatin and combinations of the above with or without the addition of steroid drugs.

Immunological agents include, but are not limited to, cytokines, chemokines, interferons, interleukins, polyclonal antibodies and monoclonal antibodies.

Compositions comprising M-DNA and MCC and a pharmaceutically acceptable carrier are prepared by uniformly and intimately bringing into association the M-DNA and the MCC with liquid carriers, with solid carriers or with both. Liquid carriers include, but are not limited to, aqueous carriers, non-aqueous carriers or both. Solid carriers include, but are not limited to, biological carriers, chemical carriers or both.

M-DNA and MCC can be administered in aqueous suspension, oil emulsion, water in oil emulsion, water-in-oil-in-water emulsion, site-specific emulsion, long-residence emulsion, sticky-emulsion, microemulsion, nanoemulsion, liposomes, microparticles, microspheres, nanospheres, nanoparticles, minipumps, and with various natural or synthetic polymers that allow for sustained release.

Further, M-DNA and MCC can be used with any one, all, or any combination of excipients regardless of the carrier used to present the composition to the responding cells. These include, but are not limited to, anti-oxidants, buffers, bacteriostats, suspending agents, surfactants and tensio active agents.

In an embodiment, MCC is administered as an aqueous suspension, wherein the size range of the MCC is preferably about 0.025 to 1.000 $\mu$m, more preferably from about 0.050 to 0.750 $\mu$m and most preferably from about 0.100 to 0.500 $\mu$m. The MCC is suspended in a pharmaceutically acceptable carrier such as, but not limited to, DNase-free water, saline or phosphate buffered saline (PBS) and is homogenized and submicronized by standard procedure such as, but not limited to, sonication and microfluidization. For example, lyophilized MCC is suspended in sterile water and sonicated at 20% output for 5 min (Model W-385 Sonicator, Heat Systems-Ultrasonics Inc) or microfluidized at 15,000–30,000 psi for one or more flow-throughs (Model M-110Y; Microfluidics, Newton, Mass.). The mixture is either aseptically processed or terminally sterilized. An optional therapeutic agent or stabilizing agent can be added to the MCC during submicronization or homogenization or before or after sterilization.

In an embodiment, M-DNA is administrated as an aqueous suspension in the size range preferably from about 2 to >12 000 b.p, more preferably from about 2 to 250 b.p. and most preferably from about 2 to 20 b.p. The M-DNA is suspended in a pharmaceutically acceptable carrier such as DNase-free water and is homogenized and fragmented by standard procedures such as, but not limited to, sonication and microfluidization. The mixture is aseptically processed or terminally sterilized. An optional therapeutic agent or stabilizing agent can be added to the M-DNA during sonication or homogenization or before or after sterilization For administration in a non-aqueous carrier, M-DNA or MCC are emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil. For example, DNase free phosphatidylcholine is added to DNase free triglyceride soybean oil at a ratio of 1 gram of phospholipid to 20 ml of triglyceride and is dissolved by gentle heating at 50°–60° C. Several grams of MCC are added to a dry autoclaved container and the phospholipid-triglyceride solution is added at a concentration of 20 ml per 1 gram of MCC. The suspension is incubated for 60 min. at 20° C. and is then mixed with DNase-free PBS in the ratio of 20 ml MCC suspension per liter of PBS. The mixture is emulsified by sonication at 20% output for 5 min (Model W-385 Sonicator, Heat Systems-Ultrasonics Inc.). Optionally, the emulsified mixture is homogenized by microfluidization at 15,000–30,000 psi for one or more flow-throughs (Model M-110Y; Microfluidics). The MCC emulsion is transferred to an autoclaved, capped bottle for storage at 4° C. Optionally a therapeutic agent or a stabilizing agent can be added to the M-DNA or the MCC composition during incubation, emulsification or homogenization.

M-DNA and MCC are administered in an amount effective to have an anti-neoplastic effect on cancer cells in the prostate of an animal. The dosage of M-DNA and MCC administered will depend on the stage of the prostate cancer being treated, the organs to which it may have metastasized, the particular formulation, and other clinical factors such as the size, weight and condition of the recipient and the route of administration.

Preferably, the amount of M-DNA and MCC administered is from about 0.00001 to 200 mg/kg per dose, more preferably from about 0.0001 to 100 mg/kg per dose, and most preferably from about 0.001 to 50 mg/kg per dose. Preferably, the M-DNA content of MCC is between about 0.001 and 90 mg/100 mg dry MCC, more preferably between about 0.01 and 40 mg/100 mg dry MCC and most preferably between about 0.1 and 30 mg/100 mg dry MCC. Unexpectedly, we found that at least about 3.6% of the dry weight of MCC is extractable M-DNA.

Routes of administration include, but are not limited to, oral, topical, subcutaneous, intra-prostatic, intra-muscular, intra-peritoneal, intra-venous, intra-arterial, intra-dermal, intra-thecal, intra-lesional, intra-tumoral, intra-bladder, intra-vaginal, intra-ocular, intra-rectal, intra-pulmonary, intra-spinal, transdermal, subdermal, placement within cavities of the body, nasal inhalation, pulmonary inhalation, impression into skin and electrocorporation.

Depending on the route of administration, the volume per dose is preferably about 0.001 to 100 ml per dose, more preferably about 0.01 to 50 ml per dose and most preferably about 0.1 to 30 ml per dose. M-DNA and MCC can be administered in a single dose treatment or in multiple dose treatments on a schedule and over a period of time appropriate to the stage of the prostate cancer being treated, the organs to which it has metastasized, the condition of the recipient and the route of administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of MCC and M-DNA

MCC was prepared from *M. phlei* as described in International Patent Application No. PCT/CA98/00744, which is included by reference herein. All reagents were selected to preserve the DNA.

M-DNA was prepared from *M. phlei* and from MCC as described in International Patent Application No. PCT/CA98/00744, which is included by reference herein. All reagents were selected to enhance conservation of (preserve) the DNA.

Unless stated otherwise, M-DNA and MCC were suspended in DNase-free water or in a pharmaceutically acceptable DNase-free buffer and sonicated. The particle size of MCC was evaluated during sonication by photon correlation spectroscopy (Zetasizer 3000, Malvern Instruments, Malvern, Worcester, England). The diameter of MCC decreased gradually with sonication (Table 1). The molecular weight of M-DNA was evaluated during sonication by electrophoresis in 2.0% agarose gel containing 0.5 µg/ml ethidium bromide (3 hours at 100 V). The molecular weight of M-DNA decreased gradually with sonication (Table 2).

TABLE 1

MCC diameter

| Sonication (minutes) | Z average mean (nm) |
|---|---|
| 0 | >10 000 |
| 15 | 688 |
| 30 | 507 |
| 45 | 400 |
| 60 | 366 |

TABLE 2

M-DNA molecular weight

| Sonication (minutes) | Molecular weight (b.p.) |
|---|---|
| 0 | >12 000 |
| 0.5 | <100 |
| 15 | <20 |

M-DNA and MCC did not contain endotoxins as determined using a Limulus amebocyte lysate QCL-1000 kit (BioWhittaker, Walkersville, Md.). The Limulus amebocyte lysate sensitivity of this assay is 5.5 pg endotoxin/ml.

EXAMPLE 2

Preparation of B-DNA and BCC

B-DNA and BCC are prepared from *M. smegmatis, M. fortuitous, Nocardia rubra, Nocardia asteroides, Cornybacterium parvum, M. kansaii, M tuberculosis* and *M. bovis* as in Example 1.

EXAMPLE 3

DNase I treatment

Treatment of M-DNA and MCC with DNase I was carried out as described in International Patent Application No. PCT/CA98/00744. DNase I digests both single stranded and double stranded DNA and causes almost total degradation of the DNA.

EXAMPLE 4

Cells and reagents

Human PC3 and DU-145 androgen-independent and LNCaP androgen-dependent prostate cancer cells were obtained from the ATCC (#CRL-1435, HTB-81 and CRL-1740, respectively). Primary human prostate epithelial cells (PrEc) were obtained from Clonetics (#CC-2555, Walkersville, Md., USA). All cell lines were cultured as recommended by the supplier. PC3, DU-145, LNCaP and PrEc cells were seeded at $3 \times 10^5$ cells/ml of growth medium in 6-well flat bottom microplates and allowed to grow for 24 h at 37° C. in 5% $CO_2$. At 24 h, growth medium was replaced with growth medium containing M-DNA or MCC.

EXAMPLE 5

Inhibition of prostate cancer cell proliferation by MCC

Cell proliferation was determined using dimethylthiazol-diphenyltetrazolium bromide (MTT) reduction (Mosman et al. J. of Immunol. Meth. 65:55, 1983).

PC3, DU-145 and LNCaP prostate cancer cells and PrEc prostate epithelial cells were incubated with 0, 0.01, 0.10, 1, 10 and 100 µg/ml of MCC. After 48 h, 100 µl of MTT in 5 mg/ml phosphate buffered saline was added to each well and incubation was continued for 4 h. Medium was then aspirated from each well, 1 ml of acidified isopropyl alcohol was added, and reduced MTT was solubilized by mixing. The absorbence of the reaction product was determined at 570 nm. MCC at 1, 10 and 100 µg/ml inhibited proliferation of androgen-dependent LNCaP prostate cancer cells and of androgen-independent PC3 and DU-145 prostate cancer cells, but did not inhibit proliferation of PrEc normal prostate cells (FIG. 1).

These data demonstrate that MCC inhibits proliferation of both androgen-independent and androgen-dependent prostate cancer cells in the absence of immune effector cells. MCC does not inhibit proliferation of normal prostate cells.

EXAMPLE 6

Inhibition of prostate cancer cell proliferation by M-DNA

Figure 2:
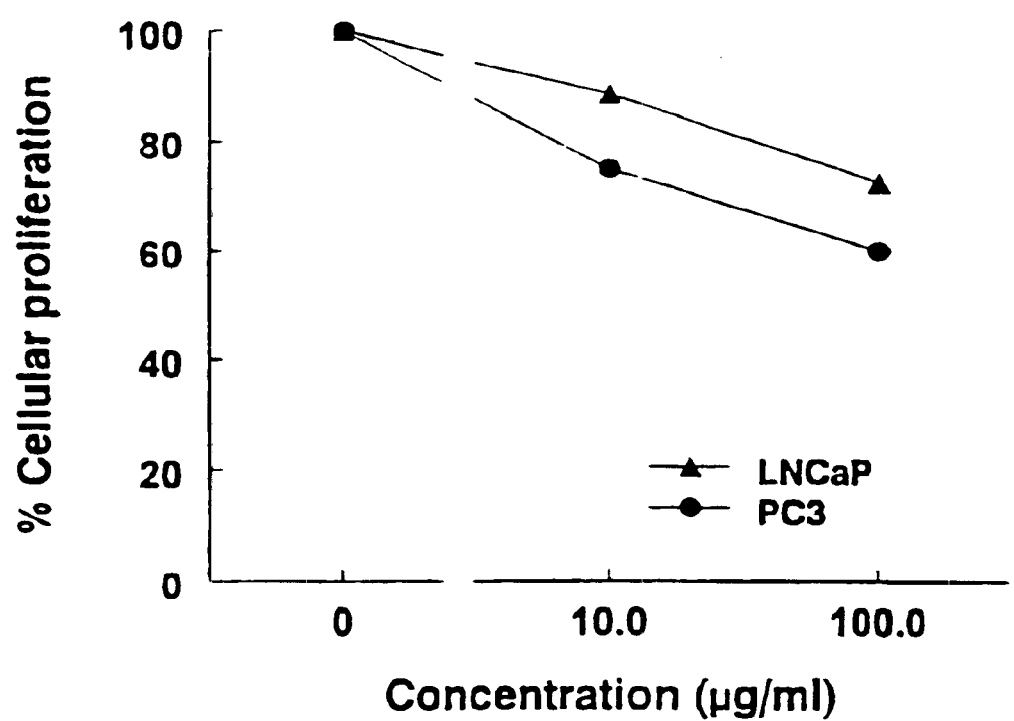
FIG. 2. Inhibition of proliferation of LNCaP and PC3 human prostate cancer cells by M-DNA.

PC3 and LNCaP prostate cancer cells were incubated with 10 and 100 µg/ml of M-DNA. Cell proliferation was determined as in Example 5. M-DNA at 10 and 100 µg/ml inhibited proliferation of PC3 prostate cancer cells (FIG. 2). These data demonstrate that M-DNA inhibits proliferation of androgen-dependent and androgen-independent prostate cancer cells in the absence of immune effector cells.

EXAMPLE 7

Inhibition of prostate cancer cell proliferation by MCC and by DNase I treated MCC PC3 prostate cancer cells were incubated with 1 Unit/ml DNase I, with 1 µg/ml MCC and with 1 µg/ml DNase I treated MCC.

Figure 3:
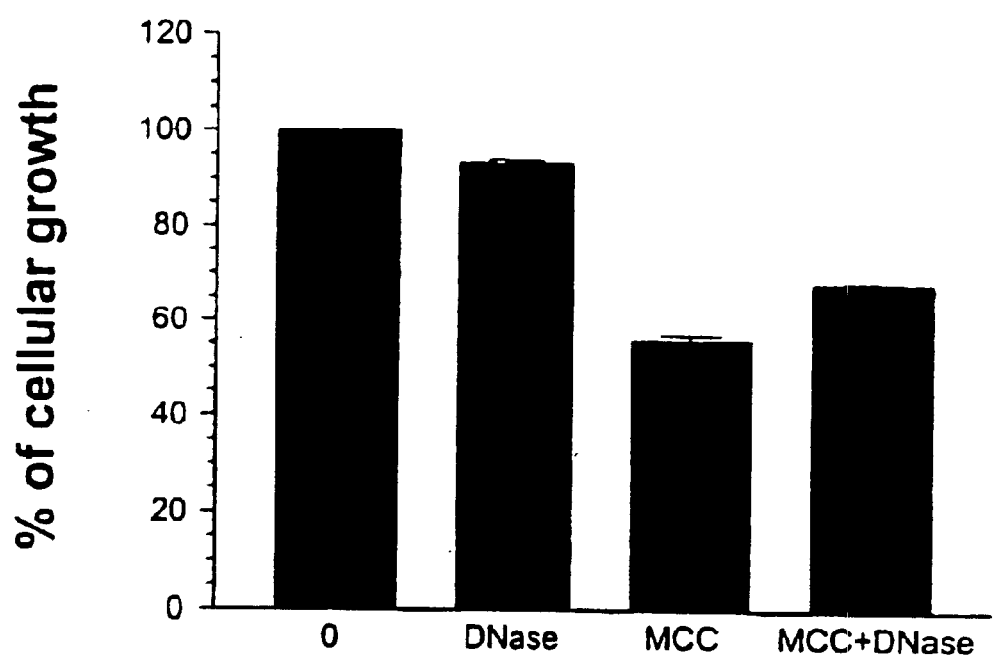
FIG. 3. Inhibition of proliferation of PC3 human prostate cancer cells by MCC and by DNase I treated MCC.

DNase I inhibited proliferation PC3 cancer cells about 5%, MCC inhibited proliferation PC3 cancer cells about 50% and DNase I treated MCC inhibited proliferation of PC3 cancer cells about 30% (FIG. 3).

These data demonstrate that MCC inhibits proliferation of androgen-independent prostate cancer cells in the absence of immune effector cells. Further, these data demonstrate that treatment of MCC with DNase I reduces the anti-proliferative effect of MCC.

EXAMPLE 8

Induction of apoptosis as indicated by morphological changes

Morphological changes indicative of cell death by apoptosis include condensation of nuclear chromatin, cell shrinkage, nuclear disintegration, plasma membrane blebbing and the formation of membrane-bound bodies (Wyllie et al. Int. Rev. Cytol. 68:251,1980).

Figure 4:
FIG. 4. Morphological changes in PC3 human prostate cancer cells after treatment with MCC.
Figure 4:

PC3 prostate cancer cells were incubated with 0 and with 200 µg/ml of MCC for 48 h. Images were collected on a light microscope with a 40×2.5 NA Apochromat objective. Cells incubated with 0 µg/ml MCC exhibited normal morphology, whereas cells incubated with 200 µg/ml MCC exhibited striking morphological changes indicative of cell death by apoptosis (FIG. 4).

These date demonstrate that MCC induces apoptosis in androgen-independent prostate cancer cells in the absence of immune effector cells.

EXAMPLE 9

Induction of apoptosis as indicated by DNA fragmentation

Fragmentation of cellular DNA into nucleosome-sized fragments by the activation of endogenous endonucleases is characteristic of cells undergoing apoptosis (Wyllie A. H. Nature 284:555, 1981; Newell et al. Nature 357:286, 1990).

During routine monolayer culture of PC3 cells, a considerable number of cells detached from the plastic surface of the tissue culture wells and floated in the medium (Palayoor et al., Radiation Res. 148:105, 1997). After 48 hours of treatment with MCC, the proportion of detached cells increased. Therefore, DNA fragmentation was analyzed both in detached and in attached PC3 cells (Smith et al. Nature 337:795, 1989).

Detached cells were collected and centrifuged at 350×G for 5 min. The pellet of detached cells and the remaining attached cells were lysed in 50 µl of buffer containing 50 mM Tris-HCl (pH 8.0), 10 mM EDTA, 0.5% (w/v) sodium lauryl sarcosinate (SDS) and 0.5 mg/ml proteinase K (Sigma-Aldrich Canada, Oakville, Ontario) at 55° C. for 1 h. Ten µl of 0.5 mg/ml RNase A (Sigma-Aldrich Canada) was added to each sample and the incubation was continued for 1 h. Samples were heated to 65° C. and 10 µl of 10 mM EDTA (pH 8.0) containing 1% (w/v) low-gelling-temperature agarose, 0.25% (w/v) bromophenol blue, 40% (w/v) sucrose was mixed with each sample. The samples were electrophoresed at 100 V for 3 h in a 2% agarose gel containing Tris-borate/EDTA buffer (TBE). The DNA was visualized under UV transillumination using ethidium bromide staining.

Figure 5:
FIG. 5. Induction of DNA fragmentation in PC3 human prostate cancer cells by MCC.

Detached and attached PC3 prostate cancer cells were incubated for 48 h with 0 and 100 µg/ml MCC. Detached cells treated with 100 µg/ml MCC showed significant DNA fragmentation (FIG. 5, lanes 3 and 4), whereas detached cells treated with 0 µg/ml MCC showed no fragmentation (FIG. 5, lane 1). Attached cells treated with 100 µg/ml MCC showed no DNA fragmentation (FIG. 5, lane 2).

These data show that MCC induces apoptosis, as indicated by DNA fragmentation, in detached androgen-independent prostate cancer cells in the absence of immune effector cells.

EXAMPLE 10

Induction of apoptosis as indicated by NuMA release

The induction of apoptosis may also be demonstrated by the solubilization and release of nuclear matrix(NuMA) protein. LNCaP prostate cancer cells were incubated for 48 h with 0, 100, 200 and 300 µg/ml MCC while PC3 prostate cancer cells were incubated for 48 h with 0, 100 and 300 µg/ml MCC. Medium was drawn off, centrifuged at 10,000×G and the supernatant was frozen at −20° C. until assayed for NuMA (Miller et al. Biotech. 15:1042, 1993).

Figure 6A:
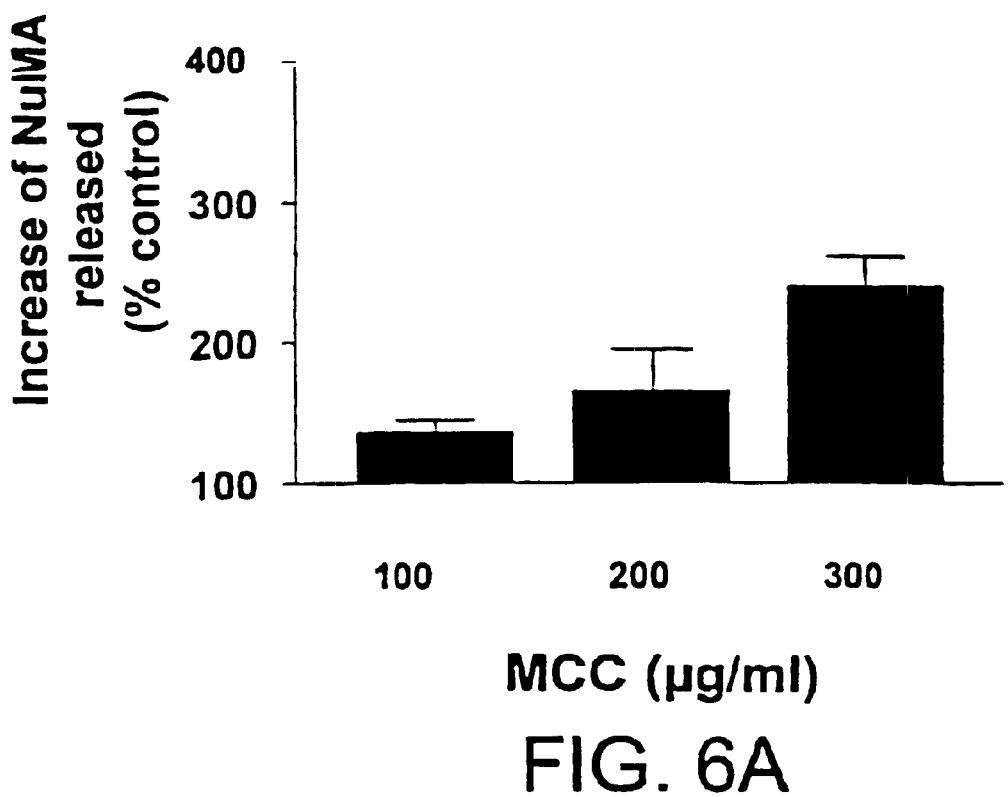
FIG. 6. Release of NuMA from (A) LNCaP and (B) PC3 human prostate cancer cells by MCC.
Figure 6B:
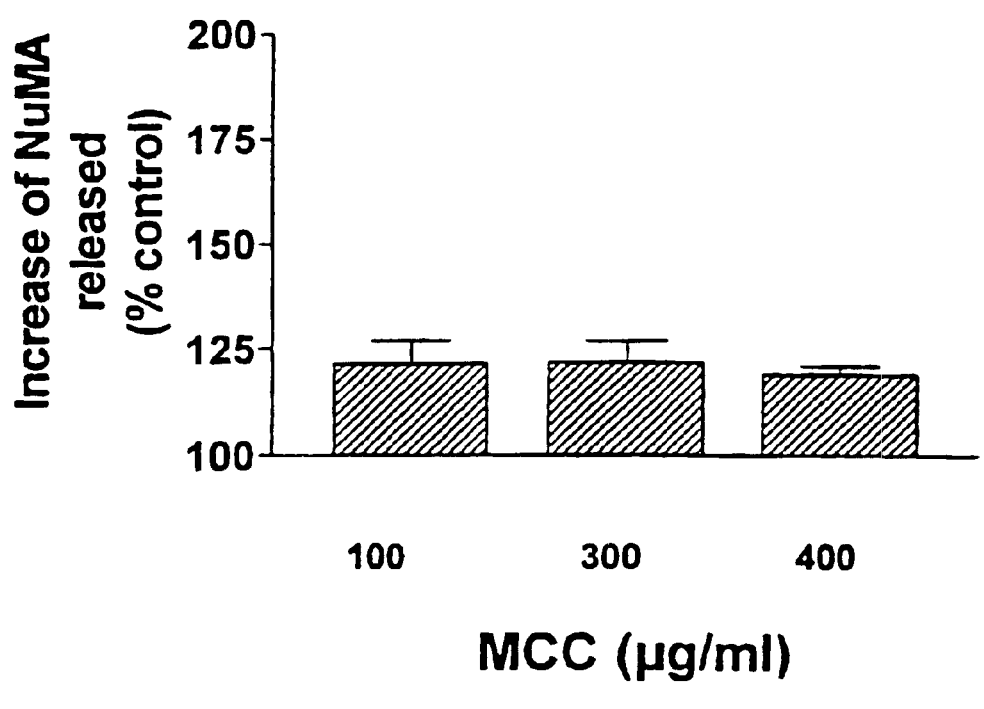

LNCaP prostate cancer cells treated with 100, 200, or 300 µg/ml MCC released 20%, 50% and 135%, respectively, more NuMA proteins into the medium than did cells treated with 0 µg/ml MCC (FIG. 6A). PC3 prostate cancer cells treated with 100 and 300 µg/ml MCC released 24% more NuMA proteins into the medium than did cells treated with 0 µg/ml MCC (FIG. 6B). These date demonstrate that MCC induces apoptosis, as indicated by NuMA release, in androgen-independent prostate cancer cells in the absence of immune effector cells.

EXAMPLE 11

Effect of MCC and M-DNA on IL-12 and TNF-α synthesis by monocytes and LNCaP cells Human monocytic THP-1 cells were obtained from the ATCC and were cultured as recommended by the supplier. THP-1 cells ($1 \times 10^6$ cells/ml) and LNCaP cells ($3 \times 10^5$ cells/ml) were incubated with 0, 0.1 and 10 µg/ml MCC for 48 hours in 5% $CO_2$ in 6-well flat bottom microplates. At 48 hours, supernatants were collected and the presence of IL-12 and TNF-α was determined using commercial ELISA kits (Biosource, Camarillo, Calif., USA). MCC and M-DNA induced synthesis of IL-12 (Table 3) and TNF-α Table 4 by immune system cells, THP-1 monocytes, and by LNCaP prostate tumor cells. The cytokines IL-12 and TNF-α both have been demonstrated to have anti-neoplastic activity against a range of cancer cells, including prostate cancer cells (Izquierdo et al. Anticancer Drugs 7: 275, 1996; Sensibar et al. Cancer Res. 55:2431, 1995).

TABLE 3

Induction of IL-12 by MCC and M-DNA

| Cells | No treatment | MCC (μg/ml) | | | M-DNA (μg/ml) | | |
|---|---|---|---|---|---|---|---|
| | | 0.1 | 1.0 | 10.0 | 0.1 | 1.0 | 10.0 |
| THP-1 | 3.3 | 148.9 | 1080.3 | 1032.0 | 132.5 | 949.8 | 925.7 |
| LNCaP | 0.1 | 1.1 | 31.3 | 103.6 | 0.9 | 5.4 | 40.0 |

TABLE 4

Induction of TNF-α by MCC and M-DNA

| Cells | No treatment | MCC (μg/ml) | | | M-DNA (μg/ml) | | |
|---|---|---|---|---|---|---|---|
| | | 0.1 | 1.0 | 10.0 | 0.1 | 1.0 | 10.0 |
| THP-1 | 3.3 | 245.4 | 390.0 | 329.7 | 230.0 | 360.3 | 315.6 |
| LNCaP | 0.1 | 186.3 | 338.7 | 284.6 | n.d | n.d | n.d |

EXAMPLE 12
Effects of MCC, M-DNA and DNase I treated MCC on PC3 tumors in mice Androgen-independent PC3 prostate cancer cells are implanted subcutaneously into 40 male nude BALB/c mice and allowed to grow until palpable (0.1 to 0.5 cm in diameter). The mice are divided into 4 groups and tumor mass is measured in each mouse. The 10 mice in Group 1 each receive saline. The 10 mice in Group 2 each receive saline containing MCC. The 10 mice in Group 3 each receive saline containing M-DNA. The 10 mice in Group 4 each receive DNase I treated MCC. After 4 weeks of once per week intra-tumoral treatments, the mice are sacrificed and the tumor mass and number of metastases are determined. The mice in Group 2 and in Group 3 have less tumor mass and fewer metastases than the mice in Group 1 and in Group 4.

EXAMPLE 13
Effects of MCC and of M-DNA alone and in combination with estramustine and etoposide on PC3 tumors in mice Androgen-independent PC3 prostate cancer cells are implanted subcutaneously into 60 male nude BALB/c mice and allowed to grow until palpable (0.1 to 0.5 cm in diameter). The mice are divided into 6 groups and tumor mass is measured in each mouse. The 10 mice in Group 1 receive saline. The 10 mice in Group 2 receive MCC in saline. The 10 mice in Group 3 receive M-DNA in saline. The 10 mice in Group 4 receive estramustine and etoposide in saline. The 10 mice in Group 5 receive MCC in combination with estramustine and etoposide in saline. The 10 mice in Group 6 receive M-DNA in combination with estramustine and etoposide in saline. After 4 weeks of once per week intra-tumoral treatment the mice are sacrificed and tumor mass and number of metastases are determined. The mice in Group 1 have the most tumor mass. The mice in Group 4 have less tumor mass than the mice in Group 1. The mice in Group 2 and Group 3 have less tumor mass than the mice in Group 4. The mice in Group 5 and in Group 6 have the least tumor mass.

EXAMPLE 14
Effects of MCC, M-DNA and DNase I treated MCC on LNCaP tumors in mice Androgen-dependent LNCaP prostate cancer cells are implanted subcutaneously into 40 male nude BALB/c mice and allowed to grow until palpable (0.1 to 0.5 cm in diameter). The mice are divided into 4 groups and tumor mass is measured in each mouse. The 10 mice in Group 1 each receive saline. The 10 mice in Group 2 each receive saline containing MCC. The 10 mice in Group 3 each receive saline containing M-DNA. The 10 mice in Group 4 each receive DNase I treated MCC. After 4 weeks of once per week intra-tumoral treatment the mice are sacrificed and the tumor mass and number of metastases are determined. The mice in Group 2 and in Group 3 have less tumor mass and fewer metastases than the mice in Group 1 and in Group 4.

EXAMPLE 15
Effects of MCC and of M-DNA alone and in combination with flutamide on LNCaP tumors in mice Androgen-dependent LNCaP prostate cancer cells are implanted subcutaneously into 60 male nude BALB/c mice and allowed to grow until palpable (0.1 to 0.5 cm in diameter). The mice are divided into 6 groups and tumor mass is measured in each mouse. The 10 mice in Group 1 receive saline. The 10 mice in Group 2 receive MCC in saline. The 10 mice in Group 3 receive M-DNA in saline. The 10 mice in Group 4 receive flutamide in saline. The 10 mice in Group 5 receive MCC in combination with flutamide in saline. The 10 mice in Group 6 receive M-DNA in combination with flutamide in saline. After 4 weeks of once per week intra-tumoral treatment the mice are sacrificed and the tumor mass and number of metastases are determined. The mice in Group 1 have the most tumor mass. The mice in Group 4 have less tumor mass than the mice in Group 1. The mice in Group 2 and Group 3 have less tumor mass than the mice in Group 4. The mice in Group 5 and in Group 6 have the least tumor mass.

It should be understood, of course, that the foregoing relates only to a preferred embodiment of the present invention and that numerous modifications or alterations may be made therein without departing from the spirit and the scope of the invention as set forth in the appended claims.

We claim:

1. A method of inhibiting proliferation of prostate cancer cells in an animal or human having prostate cancer, comprising administering at the prostate cancer cells a composition comprising:
    (a) mycobacterial DNA (B-DNA) obtained from a disrupted mycobacterium using DNase-free reagents in order to at least partially preserve the DNA; and
    (b) a pharmaceutically acceptable carrier
in an amount effective to inhibit proliferation of said prostate cancer cells.

2. The method of claim 1, wherein the mycobacterial DNA is obtained from *M. smegmatis, M. kansaii, M. fortuitum, M. tuberculosis, M. bovis, M. vaccae, M. avium* or *M. phlei*.

3. The method of claim 1, wherein the mycobacterial DNA (B-DNA) is obtained from *M. phlei*.

4. The method of claim 1, wherein the pharmaceutically acceptable carrier is mycobacterial cell wall (BCC).

5. The method of claim 4, wherein the mycobacterial DNA (B-DNA) is preserved and complexed on the mycobacterial cell wall (BCC).

6. The method of claim 1, wherein the pharmaceutically acceptable carrier is *M. phlei* cell wall (MCC).

7. The method of claim 6, wherein *M. phlei* DNA is preserved and complexed on the *M. phlei* cell wall (MCC).

8. The method of claim 1, wherein the prostate cancer is hormone-sensitive prostate cancer.

9. The method of claim 8, wherein the hormone is an androgen.

10. The method of claim 9, wherein the androgen is testosterone.

11. A method of inhibiting proliferation of prostate cancer cells in an animal or human having prostate cancer, comprising administering at the prostate cancer cells a composition comprising:
  (a) mycobacterial DNA (B-DNA) obtained from a disrupted mycobacterium using DNase-free reagents in order to at least partially preserve the DNA; and
  (b) a pharmaceutically acceptable carrier
in an amount effective to inhibit proliferation of said prostate cancer cells, wherein the inhibition of proliferation of said prostate cancer cells is caused by induction of apoptosis in the prostate cancer cells, induction of cytokine synthesis in the prostate cancer cells, or induction of cytokine synthesis by immune cells in the prostate.

12. The method of claim 11, wherein the cytokine is IL-12 or TNF-α.

13. The method of claim 1, wherein the pharmaceutically acceptable carrier is a solid carrier, a liquid carrier, or combination of a solid and liquid carrier.

14. The method of claim 1, further comprising administration of anti-androgenic agents, chemotherapeutic agents, steroids, or immunological agents.

15. A method of inhibiting proliferation of prostate cancer cells in an animal or human having prostate cancer, comprising administering at the prostate cancer cells a composition comprising:
  (a) mycobacterial DNA (B-DNA) obtained from a disrupted mycobacterium using DNase-free reagents in order to at least partially preserve the DNA, wherein the mycobacterial DNA is preserved and complexed on mycobacterial cell wall (BCC); and,
  (b) a pharmaceutically acceptable carrier
in an amount effective to inhibit proliferation of said prostate cancer cells.

16. The method of claim 15, wherein the mycobacterial DNA is obtained from *M. smegmatis, M. kansaii, M. fortuitum, M. tuberculosis, M. bovis, M. vaccae, M. avium* or *M. phlei*.

17. The method of claim 15, wherein the mycobacterial DNA is obtained from *M. phlei*.

18. The method of claim 15, wherein the mycobacterial cell wall is *M. phlei* cell wall (MCC).

19. The method of claim 15, wherein the prostate cancer is hormone-sensitive prostate cancer.

20. The method of claim 19, wherein the hormone is an androgen.

21. The method of claim 20, wherein the androgen is testosterone.

22. The method of claim 15, wherein the inhibition of proliferation of said prostate cancer cells is caused by induction of apoptosis in the prostate cancer cells, induction of cytokine synthesis in the prostate cancer cells, or induction of cytokine synthesis by immune cells in the prostate.

23. A method of inhibiting proliferation of prostate cancer cells in an animal or human having prostate cancer, comprising administering at the prostate cancer cells a composition comprising:
  (a) mycobacterial DNA (B-DNA) obtained from a disrupted mycobacterium using DNase-free reagents in order to at least partially preserve the DNA, wherein the mycobacterial DNA is preserved and complexed on mycobacterial cell wall (BCC); and,
  (b) a pharmaceutically acceptable carrier
in an amount effective to inhibit proliferation of said prostate cancer cells, wherein the inhibition of proliferation of said prostate cancer cells is caused by induction of apoptosis in the prostate cancer cells, induction of cytokine synthesis in the prostate cancer cells, or induction of cytokine synthesis by immune cells in the prostate.

24. The method of claim 15, wherein the pharmaceutically acceptable carrier is a solid carrier, a liquid carrier, or a combination of a solid and liquid carrier.

25. The method of claim 15, further comprising administration of anti-androgenic agents, chemotherapeutic agents, steroids, or immunological agents.

26. A method of inhibiting proliferation of prostate cancer cells in an animal or human having prostate cancer, comprising administering at the prostate cancer cells a composition comprising:
  (a) a predetermined amount of mycobacterial DNA (B-DNA) obtained from a disrupted mycobacterium using DNase-free reagents in order to at least partially preserve the DNA; and,
  (b) a pharmaceutically acceptable carrier
in an amount effective to inhibit proliferation of said prostate cancer cells, wherein the amount of B-DNA administered is from about 0.00001 to about 200 mg/kg per dose.

27. The method of claim 26, wherein the amount of B-DNA administered is from about 0.0001 to about 100 mg/kg per dose.

28. The method of claim 26, wherein the amount of B-DNA administered is from about 0.001 to about 50 mg/kg per dose.

29. A method of inhibiting proliferation of prostate cancer cells in an animal or human having prostate cancer, comprising administering at the prostate cancer cells a composition comprising:
  (a) *M. phlei* DNA (M-DNA) obtained from a disrupted *M. phlei* mycobacterium using DNase-free reagents in order to at least partially preserve the DNA; and,
  (b) a pharmaceutically acceptable carrier
in an amount effective to inhibit proliferation of said prostate cancer cells.

30. A method of inhibiting proliferation of prostate cancer cells in an animal or human having prostate cancer, comprising administering at the prostate cancer cells a composition comprising:
  (a) *M. phlei* DNA (M-DNA) obtained from a disrupted *M. phlei* mycobacterium using DNase-free reagents in order to at least partially preserve the DNA; and,
  (b) a pharmaceutically acceptable carrier
in an amount effective to inhibit proliferation of said prostate cancer cells, wherein the inhibition of proliferation of said prostate cancer cells is caused by induction of apoptosis in the prostate cancer cells, induction of cytokine synthesis in the prostate cancer cells, or induction of cytokine synthesis by immune cells in the prostate.

31. A method of inhibiting proliferation of prostate cancer cells in an animal or human having prostate cancer, comprising administering at the prostate cancer cells a composition comprising:
  (a) *M. phlei* DNA (M-DNA) obtained from a disrupted *M. phlei* mycobacterium using DNase-free reagents in order to at least partially preserve the DNA, wherein the *M. phlei* DNA is preserved and complexed on *M. phlei* cell wall (MCC); and,
  (b) a pharmaceutically acceptable carrier
in an amount effective to inhibit proliferation of said prostate cancer cells.

32. A method of inhibiting proliferation of prostate cancer cells in an animal or human having prostate cancer, comprising administering at the prostate cancer cells a composition comprising:
  (a) *M. phlei* DNA (M-DNA) obtained from a disrupted *M. phlei* mycobacterium using DNase-free reagents in order to at least partially preserve the DNA; and,
  (b) a pharmaceutically acceptable carrier in an amount effective to inhibit proliferation of said prostate cancer cells, wherein the inhibition of proliferation of said prostate cancer cells is caused by induction of apoptosis in the prostate cancer cells, induction of cytokine synthesis in the prostate cancer cells, or induction of cytokine by immune cells in the prostate.

33. A method of inhibiting proliferation of prostate cancer cells in an animal or human having prostate cancer, comprising administering at the prostate cancer cells a composition comprising:
  (a) a predetermined amount of *M. phlei* DNA (M-DNA) obtained from a disrupted *M. phlei* mycobacterium using DNase-free reagents in order to at least partially preserve the DNA; and,
  (b) a pharmaceutically acceptable carrier in an amount effective to inhibit proliferation of said prostate cancer cells, wherein the amount of M-DNA administered is from about 0.00001 to about 200 mg/kg per dose.

* * * * *